(12) United States Patent
Chen et al.

(10) Patent No.: US 10,517,991 B2
(45) Date of Patent: Dec. 31, 2019

(54) IRON BASED AND ABSORBABLE IMPLANTED MEDICAL DEVICE AND PREFABRICATED TUBE AND PREPARATION METHOD THEREFOR

(71) Applicant: Lifetech Scientific (Shenzhen) Co., Ltd., Shenzhen (CN)

(72) Inventors: Xianmiao Chen, Shenzhen (CN); Wenjiao Lin, Shenzhen (CN); Xiangdong Liu, Shenzhen (CN); Deyuan Zhang, Shenzhen (CN)

(73) Assignee: Lifetech Scientific (Shenzhen) Inc, Shenzhen (CN)

( * ) Notice: Subject to any disclaimer, the term of this patent is extended or adjusted under 35 U.S.C. 154(b) by 76 days.

(21) Appl. No.: 15/743,027

(22) PCT Filed: Jun. 29, 2016

(86) PCT No.: PCT/CN2016/087602
§ 371 (c)(1),
(2) Date: Jan. 9, 2018

(87) PCT Pub. No.: WO2017/016367
PCT Pub. Date: Feb. 2, 2017

(65) Prior Publication Data
US 2018/0221536 A1 Aug. 9, 2018

(30) Foreign Application Priority Data
Jul. 24, 2015 (CN) .......................... 2015 1 0444635

(51) Int. Cl.
*A61L 27/04* (2006.01)
*A61L 29/02* (2006.01)
(Continued)

(52) U.S. Cl.
CPC .............. *A61L 27/042* (2013.01); *A61F 2/06* (2013.01); *A61F 2/24* (2013.01); *A61L 29/02* (2013.01); *C22C 38/00* (2013.01)

(58) Field of Classification Search
CPC ...... A61F 2/82; A61F 2/86; A61F 2/24; A61F 2/06; A61L 31/148; A61L 27/042; A61L 29/02; C23C 8/38
See application file for complete search history.

(56) References Cited

U.S. PATENT DOCUMENTS

2015/0151027 A1* 6/2015 Zhang ...................... C23C 8/36
623/1.15
2015/0182674 A1* 7/2015 Schaffer .................. C22C 38/04
623/1.38
2015/0297370 A1* 10/2015 Hanada ................. A61L 31/022
623/1.15

FOREIGN PATENT DOCUMENTS

CN 1664154 9/2005
CN 102695529 9/2012
(Continued)

OTHER PUBLICATIONS

International Search Report dated Oct. 9, 2016 for PCT/CN2016/087602.

*Primary Examiner* — Jason-Dennis N Stewart
(74) *Attorney, Agent, or Firm* — Raymond Sun

(57) ABSTRACT

An iron based and absorbable implanted prefabricated tube (1) for medical device and preparation method therefor, and a medical device prepared by the prefabricated tube and preparation method therefor. The average nitrogen content of nitrogen in the prefabricated tube is from 0.04-0.4 wt. % or 0.02-0.04 wt. %. The prefabricated tube can be cut along the length direction directly by laser or by machining to obtain multiple absorbable implanted medical devices.

24 Claims, 1 Drawing Sheet

(51) Int. Cl.
*A61F 2/06* (2013.01)
*A61F 2/24* (2006.01)
*C22C 38/00* (2006.01)

(56) References Cited

FOREIGN PATENT DOCUMENTS

| WO | WO98556621 | 12/1998 |
| WO | WO2004029312 | 4/2004 |
| WO | WO2014011803 | 1/2014 |

* cited by examiner

IRON BASED AND ABSORBABLE IMPLANTED MEDICAL DEVICE AND PREFABRICATED TUBE AND PREPARATION METHOD THEREFOR

FIELD OF THE INVENTION

The present disclosure relates to the field of interventional medical devices, and more particularly to an iron-based absorbable implantable medical device prefabricated tube and a preparation method thereof, and an iron-based absorbable implantable medical device prepared by the same and a preparation method thereof.

BACKGROUND ART

The preparation method of an iron-based absorbable implanted medical device comprises cutting or machining a long iron-based absorbable implanted medical device prefabricated tube along the length direction into a plurality of absorbable implanted medical devices having predetermined shapes and lengths (hereinafter referred to as a forming device). The absorbable implanted medical device prefabricated tube can be obtained by drawing a large size iron-based tube blank by a supplier or buying the large size iron-based tube blank from the market and then self drawing by an iron bracket manufacturer, and the cross-sectional dimension and shape of the prefabricated tube are consistent with the cross-sectional dimension and shape of the forming device to be prepared. In order to further improve the mechanical strength of the absorbable implanted medical device, a non-metallic element can be further added into the forming device by a chemical thermal treatment, and the chemical thermal treatment includes, but is not limited to, carburizing, nitriding, and carbon-nitriding. However, the forming device has a very small size and a complex and diverse structure, and is easily deformed under the action of external forces, thus the nitriding charging furnace process of the device has a stringent requirement, a cumbersome charging process, and a low charging amount, resulting in a low nitrification efficiency of the forming device.

SUMMARY OF THE INVENTION

The present disclosure is aimed at the defects in the prior art including low nitrification efficiency and nitridation yield which is not high, and provides an iron-based absorbable implanted medical device prefabricated tube and a preparation method thereof, and an iron-based absorbable implanted medical device prepared by the same and a preparation method thereof.

The technical solution adopted for solving the technical problem of the present invention is to provide an iron-based absorbable implanted medical device prefabricated tube, the average nitrogen content of the absorbable implanted medical device prefabricated tube is from 0.04 to 0.4 wt. % or from 0.02 to 0.04 wt. %.

In the iron-based absorbable implanted medical device prefabricated tube according to one embodiment of the present disclosure, the outer diameter of the absorbable implanted medical device prefabricated tube is from 1 to 10 mm; and the wall thickness is from 0.08 to 0.6 mm.

In the iron-based absorbable implanted medical device prefabricated tube according to one embodiment of the present disclosure, the hardness of the absorbable implanted medical device prefabricated tube is from 230 to 450 HV 0.05/10.

In the iron-based absorbable implanted medical device prefabricated tube according to one embodiment of the present disclosure, the interior of the absorbable implanted medical device prefabricated tube comprises a nitrogenous solid solution.

In the iron-based absorbable implanted medical device prefabricated tube according to one embodiment of the present disclosure, the interior of the absorbable implanted medical device prefabricated tube further comprises an iron-nitrogen compound, and the iron-nitrogen compound is dispersively distributed in at least a portion of the nitrogenous solid solution.

In the iron-based absorbable implanted medical device prefabricated tube according to one embodiment of the present disclosure, the absorbable implanted medical device prefabricated tube further comprises an iron-nitrogen compound layer on the outer surface.

In the iron-based absorbable implanted medical device prefabricated tube according to one embodiment of the present disclosure, the absorbable implanted medical device prefabricated tube comprises therein a dispersively distributed compound of a strong nitride forming element and a nitrogen element.

In the iron-based absorbable implanted medical device prefabricated tube according to one embodiment of the present disclosure, the absorbable implanted medical device prefabricated tube further comprises an iron-nitrogen compound layer on the outer surface.

In the iron-based absorbable implanted medical device prefabricated tube according to one embodiment of the present disclosure, the absorbable implanted medical device prefabricated tube further comprises a nitrogenous solid solution. The compound of strong nitride forming element and nitrogen element is dispersively distributed in at least a portion of the nitrogenous solid solution.

In the iron-based absorbable implanted medical device prefabricated tube according to one embodiment of the present disclosure, the absorbable implanted medical device prefabricated tube further comprises therein an iron-base core.

In the iron-based absorbable implanted medical device prefabricated tube according to one embodiment of the present disclosure, the strong nitride forming element comprises at least one of Ti, Cr, Al, Zr, Nb, V, B, W, Mo, Hf, and Ta.

The present disclosure also provides a preparation method of the iron-based absorbable implanted medical device prefabricated tube, comprising nitriding an iron-based blank up to an average nitrogen content of from 0.04 to 0.4 wt. % or from 0.02 to 0.04 wt. %.

In the preparation method of the iron-based absorbable implanted medical device prefabricated tube according to one embodiment of the present disclosure, the preparation method further comprises drawing the iron-based blank before the nitriding until the cross-sectional shape and the cross-sectional dimension of the iron-based blank are consistent with the cross-sectional shape and cross-sectional dimension of the iron-based absorbable implanted medical device prefabricated tube.

In the preparation method of the iron-based absorbable implanted medical device prefabricated tube according to one embodiment of the present disclosure, the preparation method further comprises drawing the iron-based blank after the nitriding until the cross-sectional shape and the cross-sectional dimension of the iron-based blank are consistent with the cross-sectional shape and cross-sectional dimension of the iron-based absorbable implanted medical device prefabricated tube.

In the preparation method of the iron-based absorbable implanted medical device prefabricated tube according to one embodiment of the present disclosure, the preparation method further comprises heat-treating the nitrided iron-based blank.

In the preparation method of the iron-based absorbable implanted medical device prefabricated tube according to one embodiment of the present disclosure, the preparation method further comprises heat-treating followed by cooling the nitrided iron-based blank, and the cooling rate in cooling is not less than 10 K/s.

In the preparation method of the iron-based absorbable implanted medical device prefabricated tube according to one embodiment of the present disclosure, the outer diameter of the iron-based absorbable implanted medical device prefabricated tube is from 1 to 10 mm; and the wall thickness is from 0.08 to 0.6 mm.

In the preparation method of the iron-based absorbable implanted medical device prefabricated tube according to one embodiment of the present disclosure, the drawing passes of the drawing comprise one mandrel drawing and one mandrel-less drawing.

In the preparation method of the iron-based absorbable implanted medical device prefabricated tube according to one embodiment of the present disclosure, the drawing coefficient in the mandrel drawing is from 1.2 to 2.5; or the drawing coefficient in the mandrel drawing is from 1.5 to 2.0.

In the preparation method of the iron-based absorbable implanted medical device prefabricated tube according to one embodiment of the present disclosure, the drawing coefficient in the mandrel-less drawing is about 1 or slightly greater than 1.

In the preparation method of the iron-based absorbable implanted medical device prefabricated tube according to one embodiment of the present disclosure, the drawing passes are further supplemented by an annealing passes.

In the preparation method of the iron-based absorbable implanted medical device prefabricated tube according to one embodiment of the present disclosure, the annealing temperature in the annealing passes is from 500° C. to 750° C.

In the preparation method of the iron-based absorbable implanted medical device prefabricated tube according to one embodiment of the present disclosure, the annealing pass is followed by a cooling pass, and the cooling rate in the cooling pass is not less than 10 K/s.

In the preparation method of the iron-based absorbable implanted medical device prefabricated tube according to one embodiment of the present disclosure, the iron-based blank is a pure iron with a content of all impurity elements being smaller than or equal to 0.5 wt. %; or iron alloy with a content of all alloying elements being smaller than or equal to 3 wt. % and without strong nitride forming elements; or iron alloy with a content of all alloying elements being smaller than or equal to 3 wt. % and a total content of strong nitride forming elements being greater than or equal to 0.05 wt. %.

In the preparation method of the iron-based absorbable implanted medical device prefabricated tube according to one embodiment of the present disclosure, the carbon content of all the impurity elements in the pure iron is smaller than or equal to 0.022%; and the carbon content of all the alloying elements in the iron alloy is smaller than or equal to 0.45 wt. %.

The present disclosure also provides a preparation method of the iron-based absorbable implanted medical device, comprising molding-processing the iron-based absorbable implanted medical device prefabricated tube with an average nitrogen content of from 0.04 to 0.4 wt. % or from 0.02 to 0.04 wt. % along the length direction into a plurality of iron-based absorbable implanted medical devices.

In the preparation method of the iron-based absorbable implanted medical device according to one embodiment of the present disclosure, the preparation method further comprises nitriding an iron-based blank up to an average nitrogen content of from 0.04 to 0.4 wt. % or from 0.02 to 0.04 wt. %, to prepare the iron-based absorbable implanted medical device prefabricated tube.

In the preparation method of the iron-based absorbable implanted medical device according to one embodiment of the present disclosure, the preparation method further comprises drawing the iron-based blank before nitriding the iron-based blank until the cross-sectional shape and the cross-sectional dimension of the iron-based blank are consistent with the cross-sectional shape and cross-sectional dimension of the prefabricated tube. or drawing the nitrided iron-based blank the iron-based blank until the cross-sectional shape and the cross-sectional dimension of the iron-based blank are consistent with the cross-sectional shape and cross-sectional dimension of the iron-based absorbable implanted medical device prefabricated tube.

In the preparation method of the iron-based absorbable implanted medical device according to one embodiment of the present disclosure, the preparation method further comprises heat-treating the nitrided iron-based blank the iron-based blank and drawing the heat-treated iron-based blank until the cross-sectional shape and the cross-sectional dimension of the iron-based blank are consistent with the cross-sectional shape and cross-sectional dimension of the iron-based absorbable implanted medical device prefabricated tube.

In the preparation method of the iron-based absorbable implanted medical device according to one embodiment of the present disclosure, the preparation method further comprises heat-treating the nitrided iron-based blank.

In the preparation method of the iron-based absorbable implanted medical device according to one embodiment of the present disclosure, the preparation method further comprises heat-treating followed by cooling the nitrided iron-based blank, and the cooling rate in cooling is not less than 10 K/s.

The present disclosure provides an iron-based absorbable implanted medical device, the average nitrogen content in the absorbable implanted medical device is from 0.04 to 0.4 wt. % or from 0.02 to 0.04 wt. %.

A nitrogen element has been added into the absorbable implanted medical device prefabricated tube in the present disclosure (with an average nitrogen content of from 0.04 to 0.4 wt. % or from 0.02 to 0.04 wt. %), which can avoid later nitriding the forming device with a small size, and a complex and diverse structure, thus effectively improving the production efficiency and yield of the absorbable implanted medical device.

BRIEF DESCRIPTION OF THE DRAWINGS

The present disclosure is further described with reference to the accompanying drawings and examples, and in the drawings.

DETAILED DESCRIPTION OF THE INVENTION

Figure 1:
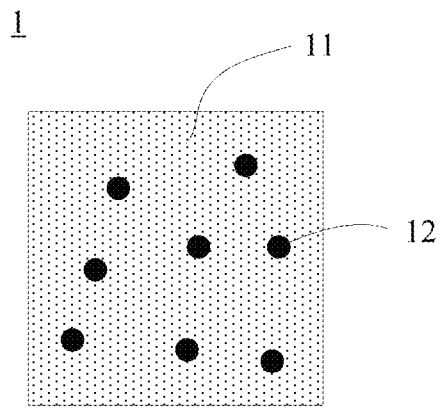
FIG. 1 shows a schematic cross-sectional view of an absorbable implanted medical device prefabricated tube according to an embodiment of the present disclosure.

The present disclosure provides an absorbable implanted medical device prefabricated tube and a preparation method thereof, and a method for preparing an absorbable implanted medical device that satisfies the mechanical property of a conventional absorbable implanted medical device by using the prefabricated tube, and the absorbable implanted medical device obtained according to the preparation method. For a clearer understanding of the technical features, objects and effects of the present disclosure, the embodiments of the present disclosure are now described in detail with reference to the accompanying drawings.

The preparation method of the iron-based absorbable implanted medical device of the present disclosure comprises processing the iron-based absorbable implanted medical device prefabricated tube (which may be referred to simply as a prefabricated tube) with an average nitrogen content of from 0.04 to 0.4 wt. % or from 0.02 to 0.04 wt. % along the length direction into a plurality of iron-based absorbable implanted medical devices, and the process includes, but is not limited to, laser cutting and machining. The cross-sectional shape and the cross-sectional dimension of the prefabricated tube are consistent with at least a portion of the cross-sectional shape and cross-sectional dimension of the forming device. The average nitrogen content (mass percent, wt. %) refers to the ratio of the total nitrogen element mass to the total mass of the component in the entire component (e.g. the prefabricated tube). The average nitrogen content of the prepared absorbable implanted medical device (which may be referred to simply as a device) is substantially from about 0.04 to 0.4 wt. % or from 0.02 to 0.04 wt. %, and due to the fact that laser cutting or machining does not have a significant impact on the nitrogen content of prefabricated tubes, the nitrogen content of the prepared device is substantially equal to the nitrogen content of the prefabricated tube. If the processing further comprises an annealing process, the nitrogen content of the device will be lower than the nitrogen content of the corresponding prefabricated tube. The prepared device includes, but is not limited to, an occluder, a lumen stent, a filter, a valve, a lung volume reduction device, and a renal artery ablation catheter.

The outer diameter of the prefabricated tube is from 1 to 10 mm, and the wall thickness is from 0.08 to 0.6 mm, the size range is only used as an example, and is not intended to limit the scope of the present disclosure, and the specific dimensions of the prefabricated tube are related to the requirements for the device to be prepared. Taking a prefabricated tube used for a lumen stent (e.g., a vascular stent, an esophageal stent, and a tracheal stent) for example, the general OD (outer diameter) is in the range of from 1 to 8 mm and the wall thickness is in the range of from 0.08 to 0.6 mm; for example, the OD of the prefabricated tube used for a coronary stent and peripheral stent may be from 1.6 to 4.2 mm, and the wall thickness may be from 0.08 to 0.21 mm; the OD of the prefabricated tube used for an abdominal main stent may be from 3 mm to 6.16 mm, and the wall thickness is from 0.25 to 0.6 mm. For the others, the OD of the preformed tube used for a filter may be about 2 mm, and the wall thickness may be about 0.28 mm; the OD of the prefabricated tube used for small incision valves may be about 8 mm, and the wall thickness may be about 0.4 mm; the OD of the prefabricated tube used for a lung volume reduction device or renal artery ablation catheter may be from 1 to 1.6 mm, and the wall thickness may be from 0.15 to 0.2 mm. In general, one of skill in the art can reasonably select the outer diameter and wall thickness of the absorbable implanted medical device prefabricated tube based on the absorbable implanted medical device that is finally prepared by the prefabricated tube.

The preparation method of the iron-based absorbable implanted medical device prefabricated tube comprises nitriding the iron-based blank up to an average nitrogen content of from 0.04 to 0.4 wt. % or from 0.02 to 0.04 wt. %. In an exemplary embodiment of the present disclosure, the preparation method comprises directly nitriding the iron-based blank up to an average nitrogen content of from 0.04 to 0.4 wt. % or from 0.02 to 0.04 wt. %, followed by further drawing the nitrided iron-based blank to obtain a prefabricated tube with a small size. In another exemplary embodiment of the present disclosure, the preparation method comprises directly drawing the iron-based blank, the cross-sectional shape and cross-sectional dimension of the drawn iron-based blank are consistent with the cross-sectional shape and cross-sectional dimension of the prefabricated tube to be prepared; then nitriding the drawn iron-base blank until a prefabricated tube with an average nitrogen content of from 0.04 to 0.4 wt. % or from 0.02 to 0.04 wt. % is obtained.

The iron-based blank is a pure iron tube or iron alloy (or called an iron-based alloy) tube, with the content of all impurity elements in the pure iron smaller than or equal to 0.5 wt. %; and the content of all alloying elements in the iron alloy is smaller than or equal to 3 wt. %. As an embodiment of the present disclosure, the carbon content in all the impurity elements of the pure iron may be smaller than or equal to 0.022%, or the carbon content of all the alloying elements of the iron alloy may be smaller than or equal to 0.45 wt. %. The iron alloy comprises an iron alloy containing a strong nitride forming element and an iron alloy containing no strong nitride forming element, and all the alloying elements of the iron alloy containing the strong nitride forming element may contain one or more strong nitride forming elements, and the total content of the strong nitride forming elements is greater than or equal to 0.05 wt. %, the above-mentioned strong nitride forming elements include, but are not limited to, Ti, Cr, Al, Zr, Nb, V, B, W and Mo.

In the preparation method of the prefabricated tube, the nitrogen element can be added to the blank by nitriding or carbon-nitriding to realize an alloying treatment of the iron-base material (comprising the iron base material before and after drawing). The nitriding method can be used as liquid nitriding, ion nitriding or gas nitriding, and the appropriate nitriding process parameters can be adjusted according to the selected nitriding method to obtain different nitrogen content and nitrogen element distribution in the iron-based material, thus obtaining an absorbable implanted medical device prefabricated tube with different mechanical properties. For example, the process parameters of liquid nitriding comprise nitriding temperature and nitriding time; the process parameters of gas nitriding comprise nitriding temperature, nitriding time, nitriding gas, and gas supply rate; the process parameters of ion nitriding comprise nitriding temperature, air pressure, bias voltage, nitriding time, and flow ratio of nitrogen to hydrogen. The range of the values for each nitriding process parameter is not enumerated here, and one of skill in the art can adjust the appropriate parameters according to the nitrogen content and nitrogen element distribution as required.

The prepared absorbable implanted medical device prefabricated tube is still pure iron or iron alloy, and the internal average nitrogen content is from 0.04 to 0.4 wt. % or from 0.02 to 0.04 wt. %, and the outer diameter is from 1 to 10 mm; and the wall thickness is from 0.08 to 0.6 mm. Since the blank comprises two blanks in which one contains a strong nitride forming element and another contains no strong nitride forming element, the following will be separately described in detail based on this.

For pure iron blank or iron alloy blank containing no strong nitride forming element, the nitrogen element added in the alloying treatment may form a nitrogenous solid solution, and the nitrogen in the nitrogenous solid solution is present as a gap atom. With the continuous infiltration of nitrogen element, the nitrogen element may further be present in at least a portion of the above-mentioned nitrogenous solid solution in the form of a finely dispersed second phase. Referring to FIG. 1, the absorbable implanted medical device prefabricated tube 1 comprises a nitrogenous solid solution 11 (hereinafter simply referred to as a solid solution) and an iron-nitrogen compound 12; and the iron-nitrogen compound 12 is dispersively distributed in at least a portion of the solid solution 11.

Figure 2:
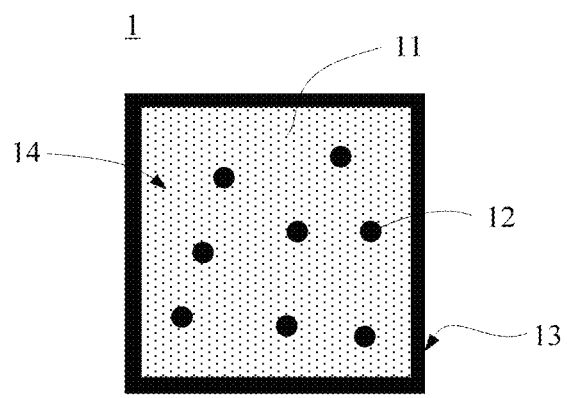
FIG. 2 shows a schematic cross-sectional view of an absorbable implanted medical device prefabricated tube according to another embodiment of the present disclosure.
Figure 3:
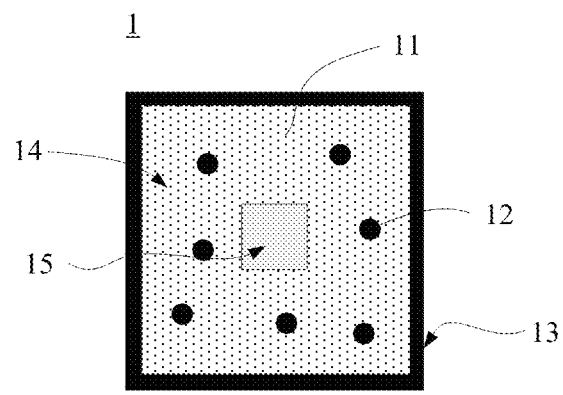
FIG. 3 shows a schematic cross-sectional view of an absorbable implanted medical device prefabricated tube according to another embodiment of the present disclosure.

Referring to FIG. 2, in an embodiment of the present disclosure, the absorbable implanted medical device prefabricated tube 1 further comprises an iron-nitrogen compound layer 13 on the outer surface thereof, and the iron-nitrogen compound layer 13 covers the solid solution 11, where the solid solution 11 is dispersively distributed with the iron-nitrogen compound 12. Since the depth of the nitrogen atom infiltrated into the blank depends on the nitriding process, when the nitrogen element is not completely infiltrated into the blank, the core of the nitrided prefabricated tube may remain as the original pure iron or iron alloy structure, which may be referred to as an iron-base core. For example, referring to FIG. 3, in another embodiment of the present disclosure, the absorbable implanted medical device prefabricated tube 1 further comprises an iron-based core 15, and the solid solution 11 covers the iron-based core, and the solid solution 11 is dispersively distributed with the iron-nitrogen compound 12, and the iron-nitrogen compound layer 13 covers the solid solution 11. In addition, in the embodiment shown in FIG. 3, it is possible that the iron-nitrogen compound layer 13 is not formed.

For the iron alloy blank containing a strong nitride forming element, in the nitriding process, the nitrogen element after infiltration may be bound to the strong nitride forming element preferentially, and if the infiltrated nitrogen content is significantly less than the content of the strong nitride forming element, the nitrogen element is barely bound to iron.

Similarly, according to the distribution of internal nitrogen element, the absorbable implanted medical device prefabricated tube containing a strong nitride forming element comprises a dispersively distributed compound strong nitride forming element and nitrogen element. Further, the absorbable implanted medical device prefabricated tube may further comprise a nitrogenous solid solution; the compound of strong nitride forming element and nitrogen element is dispersively distributed in at least a portion of the solid solution. Likewise, the absorbable implanted medical device prefabricated tube further comprises an iron-nitrogen compound layer on the outer surface, and the iron-nitrogen compound layer covers the solid solution. Of course, at this time, according to the infiltration of nitrogen element, the absorbable implanted medical device prefabricated tube may further comprise an iron-base core.

In summary, in the preparation method of the iron-based implanted medical device of the present disclosure, a nitrogen element has been added to the interior of the prefabricated tube for the preparation of the device (with an average nitrogen content of from 0.04 to 0.4 wt. % or from 0.02 to 0.04 wt. %), which thus avoids later nitriding the forming device with a small size, and a complex and diverse structure, and thus effectively improving the production efficiency and yield of the absorbable implanted medical device.

Furthermore, in the preferred preparation method of prefabricated tubes in the present disclosure, an iron-based blank is directly nitrided, and then, the nitrided iron-based blank is drawn to prepare an absorbable implanted medical device prefabricated tube, which has a size being smaller than that of the original iron-based blank. In this preparation method, as the nitrided iron-based blank is added therein with nitrogen elements (the average nitrogen content is from about 0.04 to 0.4 wt % or from 0.02 to 0.04 wt %), the overall plasticity of the tube is effectively improved. This is conducive to the implementation of subsequent drawing steps and may minimize the formation of cracks on the surface of the tube during drawing, thereby effectively improving the performance and quality of the final absorbable implanted medical device product. Furthermore, common original blanks are large-sized tubes. For example, a blank having a length of 300 mm, an outer diameter of 6 mm and a wall thickness of 0.5 mm may be selected for nitriding. Therefore, the nitriding charging of the blank is simple to operate, without too many demanding requirements; and the blank of this size may be correspondingly drawn to obtain a small-sized tube having a length of at least 2 m, and the small-sized tube may be cut to obtain hundreds of absorbable implanted medical devices. Consequently, hundreds of absorbable implanted medical devices may be obtained by a single nitriding, thus greatly improving production efficiency. Moreover, in this preferred preparation method, the drawing conducted for the nitrided iron-based blank exerts no negative influence on the work-hardening effects produced by drawing. Specifically, liquid nitriding and gas nitriding are typically conducted at a high temperature (e.g., above 500° C.), which tends to lead to annealing of iron-based blanks. Here, the drawing conducted for the nitrided iron-based blank does not weaken the work-hardening effects produced by drawing, nor does it exert any influence on hardness. Moreover, the solid-solution strengthening and dispersion strengthening of nitrogen elements may further enhance the work-hardening effects produced by drawing, thus further improving the hardening effects of the tube.

In actual nitriding processes, nitrogen atoms diffuse from the surface of a blank towards the core. Under some nitriding conditions, the cross-sectional nitrogen concentration of a nitrided tube varies along the radial direction. For example, there is a concentration gradient from the surface to the core. Uneven distribution of the nitrogen concentration will lead to differences in mechanical properties of the cross section in the radial direction, which affects the stability of mechanical properties of an absorbable implanted medical device, thus increasing the difficulty in the structural design of the absorbable implanted medical device.

In addition, the prefabricated tube for some absorbable implanted medical devices is covered on its surface with an iron-nitrogen compound layer (commonly known as a white bright layer). The iron-nitrogen compound layer is featured by high brittleness and good corrosion-resistant properties, which is unfavorable for direct application in absorbable implanted medical device products. In the prior art, the process of removing the iron-nitrogen compound layer is typically implemented after nitriding treatment. In other words, a polishing process is added to remove the iron-nitrogen compound layer after nitriding. However, the removal of the iron-nitrogen compound layer leads to obvious reduction in the size of an absorbable implanted medical device. In order to obtain the absorbable implanted medical device having a required size, the removing thickness must be controlled precisely, thereby increasing the difficulty in the size design of the absorbable implanted medical device.

In view of this, in the above preparation method of the prefabricated tubes, the nitrided iron-based blank may also be thermally treated. For example, in an exemplary preparation method of the prefabricated tubes of the present disclosure, a nitrided iron-based blank is thermally treated prior to drawing; alternatively, in another exemplary preparation method, an iron-based blank is subjected successively to drawing and nitriding before thermal treatment.

During thermal treatment, the decomposition of iron-nitrogen compounds and the even diffusion and distribution of nitrogen elements are associated with the temperature and time in the thermal treatment process. It is typically believed that the longer the time and/or the higher the temperature, the better the effects of decomposition and diffusion. In order to reduce the time of thermal treatment and/or reach better thermal treatment effects, the temperature of thermal treatment may be higher than or equal to the theoretical decomposition temperature of iron-nitrogen compounds. The phase diagram shows that the theoretical decomposition temperature of iron-nitrogen compounds is about 680° C. Therefore, if the thermal treatment temperature is higher than or approximately equal to 680° C., iron-nitrogen compounds can be decomposed more effectively in the thermal treatment process, and decomposed nitrogen elements are caused to diffuse towards the interior of the material, thus promoting the even distribution of nitrogen elements in the interior of an absorbable implanted medical device prefabricated tube. Certainly, the thermal treatment conducted at a temperature lower than the above decomposed temperature can likewise reach the effect of removing the iron-nitrogen compound layer, e.g., at 650° C. or a lower temperature. However, the time of the thermal treatment may need to be prolonged correspondingly. Those skilled in the art may reasonably select suitable thermal treatment temperature, time, atmosphere and the like according to actual requirements and situations, which will not be described herein in detail.

For the absorbable implanted medical device prefabricated tube that has been thermally treated, the iron-nitrogen compound layer on its surface is decomposed. After decomposition, nitrogen elements diffuse towards the interior of the material, and there are also a small number of nitrogen elements escaping from the absorbable implanted medical device prefabricated tube, such that its average nitrogen content is slightly decreased. Typically, the amount of escape is not obvious, and has little influence on the overall performance of the absorbable implanted medical device prefabricated tube. Additionally, the nitrogen concentration no longer has an obvious gradient, but rather, it is evenly distributed from the surface to the core. Moreover, in one specific implementation, removing or reducing the iron-nitrogen compound layer having a wear-resistant surface is conducive to subsequent drawing, which not only prevents the hard iron-nitrogen compound layer from damaging the mandrel during drawing, but also avoids surface cracks and even fractures due to excessively high surface hardness during drawing. The above thermal treatment is not intended to mechanically remove the surface of the iron-nitrogen compound layer. Therefore, the size of the tube will not change significantly in the removing process, and thus no influence will be exerted on the structural design of the absorbable implanted medical device. Moreover, the even distribution of nitrogen elements in the interior of the absorbable implanted medical device prefabricated tube may effectively improve its plasticity, thus rendering its mechanical properties even and stable.

If the average nitrogen content of the prefabricated tube is low (for example, the average nitrogen content is about or slightly greater than 0.02 wt. % and less than 0.04 wt. %), the preliminary nitrided iron-based blank has a low hardness. In view of this, the nitrided iron-based blank may be cooled after being thermally treated, and the cooling rate in this cooling process is not less than 10 K/s. Cooling at this cooling rate can inhibit the growth of iron-nitrogen compounds in the cooling process, such that iron-nitrogen compounds in the prefabricated tube are finer and more diffused. As finer iron-nitrogen compounds produce better dispersion strengthening effects, a higher hardness can be obtained at a lower nitrogen content. Meanwhile, a lower nitrogen content can improve the over-expanding plasticity of medical devices (for example, luminal stents) prepared by this prefabricated tube.

Drawing refers to the process in which an external force is applied, at the recrystallization temperature of a tube blank material (e.g., at room temperature), to the front end of a tube to be drawn to draw the tube out of a mold hole whose diameter is smaller than that of the tube so as to obtain a tube having a smaller diameter. In the present disclosure, drawing can be utilized to reduce the tube diameter, and the hardness of the tube can also be regulated to be suitable for preparing the absorbable implanted medical device. In practice, under the teachings of the present disclosure, a suitable mold may be selected based on the radial size of the absorbable implanted medical device to be prepared and in conjunction with the drawing process parameters planned to be adopted in the drawing process (e.g., the number of drawing passes and/or drawing coefficients, etc.), all of which need not be detailed here.

The drawing passes of drawing comprise at least one mandrel drawing and at least one mandrel-less drawing after the mandrel drawing, wherein the mandrel drawing may be long mandrel drawing. For example, 3-7 passes of long mandrel drawing may be adopted, followed by one mandrel-less drawing in the end. In each of the mandrel drawing processes, the drawing coefficient is: $\mu=1.2$-$2.5$. In one implementation of the present disclosure, this coefficient is preferably from 1.5 to 2.0, wherein $\mu=Q0/Q1$, $Q0$ is the cross-sectional area of an original tube (blank) before drawing, and $Q1$ is the cross-sectional area of the tube (an absorbable implanted medical device prefabricated tube) after drawing. This drawing coefficient is also referred to as the extension coefficient when being characterized using the length ratio of the tube. It should be appreciated that for a solid piece, its volume remains unchanged before and after drawing. Therefore, the cross-sectional area ratio is inversely proportional to the length ratio.

After mandrel drawing, the mandrel and the tube blank are stuck together, and demolding is required to separate the mandrel from the tube blank. Demolding comprises squeezing the tube blank to make it undergo plastic deformation, and as the mandrel does not deform because of its high hardness, it will be separated from the tube blank. As the tube blank is plastically deformed after mandrel drawing, changes occur to its surface state and outer diameter. Therefore, at least one mandrel-less drawing needs to be conducted for sizing (precisely fixing the size of the outer diameter) and eliminating deformation marks on the surface of the tube after demolding. Typically, the drawing coefficient adopted during mandrel-less drawing is about 1.0 or slightly greater than 1.0. For example, it may be from 1.01 to 1.05. Mandrel-less drawing is utilized to reduce the outer diameter of the tube blank and increase the wall thickness.

During drawing, it is common that multiple mandrel drawings need to be conducted to obtain the final required small-sized tube. If the hardness of the tube is too high after some mandrel drawing in the process, it will be unfavorable for subsequent drawing. In view of this, 1-5 annealing passes may be suitably supplemented during drawing passes, and suitably annealing the tube may mitigate the work-hardening effects, such that subsequent drawing passes can be continued. Alternatively, 1-5 annealing passes may also be suitably supplemented during drawing passes according to the hardness of the final required tube. For example, if the hardness is required to be high after drawing (e.g., 250 HV0.05/10 or above), no annealing pass is required to be set in the drawing procedure; if the hardness obtained after drawing is required to be low (e.g., less than 250 HV0.05/10), several annealing passes may be added in the drawing procedure. The timing for annealing is dependent on the tube hardness of the intermediate drawing pass. When the tube hardness of the intermediate pass ranges from 200 to 240 HV0.05/10, annealing passes may be set, and the annealing temperature may be selected to be from 500 to 750° C.

Take a luminal stent as an example. For a coronary stent, the OD (outer diameter) of the tube after drawing is generally from 2.0 to 5.0 mm; for a peripheral stent, the OD of the tube after drawing is generally from 5.0 to 14.0 mm; the pass and coefficient of drawing may be selected according to the type or model of the final absorbable implanted medical device. Drawing may be used to regulate not only the size of a tube, but also its mechanical properties. In the present disclosure, the tube after drawing has a hardness of from 230 to 450 HV0.05/10 (the Vickers hardness number measured when the tube is maintained under the test force of 0.05 kilogram force for 10 seconds).

In one specific implementation of the present disclosure, the absorbable implanted medical device prefabricated tube to be drawn has an average nitrogen content of from 0.04 to 0.4 wt. % or from 0.02 to 0.04 wt. %, such that the overall plasticity of the tube is effectively improved. This is conducive to the implementation of drawing and may minimize the formation of cracks on the surface of the tube during drawing, thereby effectively improving the performance and quality of the final absorbable implanted medical device product.

For example, still in the case of the luminal stent, the OD of the absorbable luminal stent prepared through the preparation method of absorbable implanted medical devices of the present disclosure falls within the size range of the coronary stent, the radial strength is from 100 to 160 kPa, and the over-expanding plasticity is from 30 to 45%. Currently, the mechanical property requirements for the coronary stent are generally as follows: under the condition that OD is in the range of from 2.0 to 5.0 mm, the radial strength is not less than 80 kPa, and the over-expanding plasticity is not less than 20%. Therefore, the coronary stent according to the present disclosure meets the mechanical property requirements of conventional coronary stents. Although the present disclosure has disclosed certain parameters of the coronary stent, these parameters are not intended to limit the scope of the present disclosure. On the basis of the teachings of the present disclosure, those skilled in the art may apply the above preparation method to peripheral stents and other absorbable implanted medical devices. The absorbable implanted medical device prefabricated tube and preparation method thereof based on the teachings of the present disclosure, and the absorbable implanted medical device and preparation method thereof based thereon, all fall within the scope of protection of the present disclosure.

Embodiment 1

An iron-based blank in this embodiment is a pure iron tube blank with a size of 6*0.5 (the outer diameter is 6 mm, and the wall thickness is 0.5 mm), wherein the total impurity element content of the blank is smaller than or equal to 0.5 wt. %, and the carbon content therein is smaller than or equal to 0.022%. First, the blank is directly nitrided using a liquid nitriding (also known as salt bath nitriding) method, wherein the nitriding temperature is 565° C., the nitriding time is 2 hours, and the salt bath formula is the dedicated salt for salt bath nitriding. An absorbable implanted medical device prefabricated tube obtained through nitriding comprises, from the surface towards the interior, an iron-nitrogen compound layer with a compact surface and a nitrogenous solid solution, wherein iron-nitrogen compounds are dispersively distributed in at least part of the solid solution. Salt remaining on the surface of the absorbable implanted medical device prefabricated tube is washed for nitrogen content testing. The testing is conducted with reference to the national standard GB/T20124-2006 "Steel and Iron-Determination of Nitrogen Content-Thermal Conductimetric Method After Fusion in A Current of Inert Gas", and the testing result shows that the average nitrogen content is 0.40 wt. %.

A first layered structure on the surface of the nitrided iron-based blank is a compact iron-nitrogen compound layer with high hardness, which is unfavorable for the implementation of subsequent drawing process; moreover, the nitrogen contents of the surface and core of the nitrided iron-based blank may be distributed unevenly, and it may be that the nitrogen content on the outer surface of the tube may be higher, while that in the core is lower. Therefore, in order to remove the iron-nitrogen compound layer unfavorable for drawing and achieve even distribution of nitrogen contents, thermal treatment may be conducted immediately after nitriding.

The Fe—N phase diagram shows that Fe and N may form such compounds as $Fe_4N$ and $Fe_2N$. The highest existence temperature of these iron-nitrogen compounds is 680° C., and at a temperature higher than this existence temperature, the iron-nitrogen compounds will be decomposed. After decomposition, Fe atoms and N atoms will diffuse. The driving force for diffusion is the chemical-potential gradient. In the present disclosure, Fe and N form a solid-solution phase at a temperature higher than 680° C. (i.e. that N is solid-dissolved in Fe), which do not form any compounds or lead to other phase change processes. The direction of the chemical-potential gradient is consistent with that of the concentration gradient, and the final result of diffusion is that the distribution of nitrogen elements has no concentration gradient, i.e. that components are homogenized.

The diffusion capability of atoms is associated with the temperature and time. The higher the temperature, the shorter the time required for the final homogenization of components. For example, the thermal treatment process in which thermal insulation is conducted at the temperature of 850° C. for 1 hour may be adopted. Different thermal treatment equipment may vary during the stages of temperature increase and temperature decrease. If a vacuum thermal treatment furnace is adopted, it must be vacuumed to be below 10 Pa before the temperature can be increased. When the temperature is decreased, it needs to be below about 300° C. before air may be charged, and the tube should be taken out to avoid oxidation. The tube after thermal treatment is of a fully annealed organization, and N elements in the organization are present in iron in the form of a solid-solution state and/or a fine and dispersive second phase. Fe—N compounds in the iron-nitrogen compound layer on the surface are decomposed during thermal treatment, and after decomposition, some of the N atoms escape to the vacuum atmosphere, while some diffuse from the surface to the core. Therefore, the N content obtained after thermal treatment is slightly lower than that before thermal treatment. It is detected that in the present embodiment, the N content obtained through the thermal treatment process in which thermal insulation is conducted at the temperature of 850° C. for 1 hour is 0.37 wt. %, which is slightly lower than that of 0.4 wt. % before thermal treatment.

Next, the iron-based blank after thermal treatment is drawn, wherein drawing passes comprise multiple long mandrel drawings and one mandrel-less drawing, and annealing passes may also be supplemented between the above drawing passes. For example, the adopted drawing passes include, successively: ① an outer mold of 5 mm and a mandrel of 4.4 mm are adopted for long mandrel drawing; ② an outer mold of 4.4 mm and a mandrel of 4.0 mm are adopted for long mandrel drawing; ③ annealing is conducted at the temperature of 720° C. for half an hour; ④ an outer mold of 3.5 mm and a mandrel of 3.19 mm are adopted for long mandrel drawing; ⑤ an outer mold of 2.3 mm and a mandrel of 2.02 mm are adopted for long mandrel drawing; ⑥ an outer mold of 1.795 mm and a mandrel of 1.627 mm are adopted for long mandrel drawing; and ⑦ an outer mold of 1.590 mm is adopted for mandrel-less drawing.

In order to reduce the occurrence of drawing defects, the elongation coefficients for all the drawing passes do not exceed 2.0, which are preferably about 1.5. As a metal material has a certain elastic after-effect, the outer diameter has certain resilience after the drawing with the outer mold of 1.590 mm, and actual measurements show that the outer diameter is 1.600 mm, and the wall thickness is 0.090 mm. After drawing, a tube which contains invariant components (the total impurity element content is smaller than or equal to 0.5 wt. %, wherein the carbon content is smaller than or equal to 0.022%) and has an outer diameter of 1.600 mm, a wall thickness of 0.090±0.005 mm and a hardness of 430 HV0.05/10 is obtained. The Vickers hardness test is conducted based on the testing method in GB/T4340.1-2009. Here, a load of 50 gf is adopted, and pressure is maintained for 10 seconds. Then, calculation is made based on the length of the diagonal line of indentation to obtain the Vickers hardness number of the tube.

The above prefabricated tube after drawing is subjected to laser cutting to obtain a coronary stent with a specification of 3.0*18 mm, wherein the cutting precision is ±5 μm. As the surface quality of the post-drawing prefabricated tube is high after N element alloying treatment is conducted for the raw material, and the iron-nitrogen compound layer on the surface is removed in the post-nitridation thermal treatment, chemical or electrochemical polishing may be conducted directly to obtain a required stent. The laser-cut stent is polished to the size of the finished product (for example, width of the stent rod is 90 μm, and wall thickness of the stent is 50 μm), and no crack can be observed from the inner and outer surfaces of the stent after it is polished Measurements show that the radial strength of the stent is about 120 kPa, and the over-expanding plasticity is about 25%, thus meeting the requirements of medical devices and parts thereof (e.g., stents) for radial strength and plasticity.

During the testing on the radial strength of the absorbable implanted medical device, radial pressure is evenly applied to the absorbable implanted medical device by a compression module, such that the absorbable implanted medical device is compressed and deformed evenly. It is defined that the magnitude of the applied radial pressure is the radial strength of the stent when the absorbable implanted medical device is deformed by 10% in a radial direction (in terms of outer diameter).

The testing on the plasticity of the absorbable implanted medical device is conducted according to the following example. Take a stent with the specification of OD3.0*18 mm (OD is 3.0 mm, and the tube length is 18 mm) as an example. When the stent is expanded by a matched balloon catheter of 3.0*18 mm to the nominal diameter pressure of the balloon catheter (it is typically marked on the balloon catheter, which is usually 8 atm), its inner diameter is 3.0 mm, which is the nominal diameter of the stent. When stents prepared by prefabricated tubes of different materials and having the same specification are gradually expanded from small to large by balloon catheters having different nominal diameters or by different expanding pressure, fracturing situations of the stents are observed. The biggest expanding diameter D (mm) within which a stent does not fracture during expanding is recorded, calculation is made for the equation 100*(D−3.0)/D %, and the over-expanding plasticity of the material is hereby characterized. If the biggest expanding diameter within which a stent does not fracture during expanding is greater, it is indicated that its anti-fracture properties is better, and the plasticity is higher. If a stent fractures before being expanded to 1.2 times of the nominal diameter (corresponding to 20% of over-expanding plasticity), such material is featured by excessively low plasticity under the current tube drawing process or after corresponding modification under the current tube drawing process, which cannot be used in manufacturing stents.

Embodiment 2

A blank selected in this embodiment is an iron alloy tube having a size of 6*0.5 (the outer diameter is 6 mm, and the wall thickness is 0.5 mm). The total alloying element content of this iron alloy is smaller than or equal to 3 wt. %, and the alloying elements lack strong nitride-forming elements. For example, components of the iron alloy may be: 0.3 wt. % of C, 0.30 wt. % of Si, 0.60 wt. % of Mn, 0.025 wt. % of P, 0.025 wt. % of S, 0.25 wt. % of Ni and 0.25 wt. % of Cu, and the content of all the alloying elements is 1.75 wt. %.

The blank is nitrided using a gas nitriding method, wherein the nitriding temperature is 570° C., the nitriding time is 1 hour, the gas supply rate is 10 (the gas supply rate is gas supply amount per hour/in-furnace volume), and the nitriding gas is ammonia gas. A nitrided tube comprises a solid solution and an iron-nitrogen compound layer coated on the surface of the solid solution, wherein iron-nitrogen compounds are dispersively distributed in at least part of the solid solution. N content of the nitrided tube is tested using the same testing method as that in Embodiment 1, and the measurement shows that the average N content is 0.18 wt. %.

The nitrided tube has a compact surface, and the iron-nitrogen compound layer having a high hardness is unfavorable for the implementation of subsequent drawing processes. Moreover, the N contents of the surface and core of the nitrided tube are distributed unevenly, wherein the N content is higher on the surface, while that is lower in the core. In order to remove the iron-nitrogen compound layer on the surface and achieve even distribution of N elements in the absorbable implanted medical device prefabricated tube, the nitrided tube may be thermally treated. For example, the thermal treatment process that may be adopted is one in which thermal insulation is conducted at the temperature of 880° C. for 1 hour. The tube after thermal treatment is of a fully annealed organization, and N elements in the organization are present in the substrate in the form of a solid-solution state and/or a fine and dispersive second phase. As Fe—N compounds are decomposed during thermal treatment, after decomposition, some of the N atoms escape to the vacuum atmosphere, while some diffuse to the core. Therefore, the N content after thermal treatment is slightly lower than that before thermal treatment. It is detected that in the present embodiment, the N content obtained through the thermal treatment process in which thermal insulation is conducted at the temperature of 880° C. for 1 hour is 0.17 wt. %.

The tube after thermal treatment is drawn, wherein the drawing passes comprise multiple mandrel drawings and one mandrel-less drawing, and annealing passes may also be supplemented between the above drawing passes. The drawing passes adopted in the drawing include, successively: ① an outer mold of 5 mm and a mandrel of 4.4 mm are adopted for long mandrel drawing; ② an outer mold of 4.4 mm and a mandrel of 4.0 mm are adopted for long mandrel drawing; ③ annealing is conducted at the temperature of 720° C. for half an hour; ④ an outer mold of 3.5 mm and a mandrel of 3.19 mm are adopted for long mandrel drawing; ⑤ an outer mold of 2.3 mm and a mandrel of 2.02 mm are adopted for long mandrel drawing; ⑥ an outer mold of 1.795 mm and a mandrel of 1.627 mm are adopted for long mandrel drawing; ⑦ annealing is conducted at the temperature of 500° C. for half an hour; and ⑧ an outer mold of 1.594 mm is adopted for mandrel-less drawing.

In order to reduce the occurrence of drawing defects, the elongation coefficients for all the drawing passes do not exceed 2.0, which are preferably about 1.5. As a metal material has a certain elastic after-effect, the outer diameter has certain resilience after the drawing with the outer mold of 1.594 mm, and actual measurements show that the outer diameter is 1.600 mm, and the wall thickness is 0.090 mm. After drawing, a tube which contains invariant components (the total impurity element content is smaller than or equal to 0.5 wt. %, wherein the carbon content is smaller than or equal to 0.022%) and has an outer diameter of 1.60 mm, a wall thickness of 0.090±0.005 mm and a hardness of 250 HV0.05/10 is obtained.

The above prefabricated tube after drawing is subjected to laser cutting to obtain a coronary stent with a specification of 3.0*18 mm, wherein the cutting precision is ±5 μm. As the iron-based blank that has been subjected to N element alloying treatment is drawn, the prefabricated tube prepared therefrom has high surface quality. Moreover, as the iron-nitrogen compound layer on the surface is removed, chemical or electrochemical polishing may be conducted directly to obtain a required stent. The laser-cut stent is polished to the size of the finished product (for example, width of the stent rod is 90 μm, and wall thickness of the stent is 50 μm), and no crack can be observed from the inner and outer surfaces of the stent after it is polished. Measurements show that the radial strength of the stent is about 110 kPa, and the over-expanding plasticity is about 40%, thus meeting the requirements of medical devices and parts thereof (e.g., stents) for radial strength and plasticity.

Embodiment 3

A blank selected in this embodiment is a pure iron tube blank (with a total alloying element content being smaller than or equal to 0.5 wt. %, wherein the carbon content is smaller than or equal to 0.022%) having a size of 6*0.5 (the outer diameter is 6 mm, and the wall thickness is 0.5 mm).

The blank is nitrided with an ion nitriding method, with a nitriding temperature being 400° C., a nitrogen-hydrogen flow ratio being 1:3, an air pressure being from 300 to 500 Pa, a bias pressure being about 600 V, and a nitriding time being 120 minutes. The surface of the tube prepared through nitriding lacks a compact iron-nitrogen compound layer, including a uniform nitrogenous solid solution and an iron-nitrogen compound dispersively distributed in at least a part of the nitrogenous solid solution. The absorbable implanted medical device prefabricated tube is detected N content by adopting the same method in embodiment 1, with an average N content being 0.07 wt. %.

As the surface of the nitrided iron-based blank lacks a compact iron-nitrogen compound layer, not thermal treatment but direct drawing is needed. Drawing passes comprise multiple mandrel drawings and one mandrel-less drawing, and annealing passes may also be supplemented between the above drawing passes. The drawing passes adopted in the drawing include, successively: ① an outer mold of 5 mm and a mandrel of 4.4 mm are adopted for long mandrel drawing; ② an outer mold of 4.4 mm and a mandrel of 4.0 mm are adopted for long mandrel drawing; ③ annealing is conducted at the temperature of 530° C. for half an hour; ④ an outer mold of 3.5 mm and a mandrel of 3.19 mm are adopted for long mandrel drawing; ⑤ an outer mold of 2.3 mm and a mandrel of 2.02 mm are adopted for long mandrel drawing; ⑥ an outer mold of 1.795 mm and a mandrel of 1.627 mm are adopted for long mandrel drawing; ⑦ an outer mould of 1.594 mm is adopted for mandrel-less drawing.

In order to reduce the occurrence of drawing defects, the elongation coefficients for all the drawing passes do not exceed 2.0, which are preferably about 1.5. As a metal material has a certain elastic aftereffect, the outer diameter has certain resilience after the drawing with the outer mould of 1.594 mm, and actual measurements show that the outer diameter is 1.600 mm, and the wall thickness is 0.090 mm. After drawing, a tube which contains invariant components (the total impurity element content is smaller than or equal to 0.5 wt. %, wherein the carbon content is smaller than or equal to 0.022%) and has an outer diameter of 1.60 mm, a wall thickness of 0.090±0.005 mm and a hardness of 300 HV0.05/10 is obtained.

Laser cutting is conducted for the above prefabricated tube after drawing to obtain a coronary stent with the specification of 3.0*18 mm, wherein the cutting precision is ±5 μm. As the original material has been subjected to N element alloying treatment, the prefabricated tube prepared by drawing has high surface quality. Moreover, as the surface is free from the iron-nitrogen compound layer, chemical or electrochemical polishing may be conducted directly to obtain a required stent. The laser-cut stent is polished to the size of the finished product (for example, width of the stent rod is 90 μm, and wall thickness of the stent is 50 μm), and no crack can be observed from the inner and outer surfaces of the stent after it is polished. Measurements show that the radial strength of the stent is about 110 kPa, and the over-expanding plasticity is about 35%, thus meeting the requirements of medical devices and parts thereof (e.g., stents) for radial strength and plasticity.

Embodiment 4

A blank adopted in this embodiment is an iron alloy tube (content of the total alloying element is smaller than or equal to 3 wt. %, one or more strong nitride-forming elements are contained, which include but are not limited to Ti, Cr, Al, Zr, Nb, V, B, W and Mo, and the total content of the strong nitride-forming elements is not smaller than 0.05 wt. %) having a size of 6*0.5 (the outer diameter is 6 mm, and the wall thickness is 0.5 mm). For example, components of the iron alloy may be: 0.1 wt. % of C, 0.17 wt. % of Si, 0.50 wt. % of Mn, 0.03 wt. % of P, 0.020 wt. % of S, 0.45 wt. % of Mo and 1.0 wt. % of Cr, 0.15 wt. % of Cu and 0.25 wt. % of Ni, i.e. the content of all the alloying elements is 2.67 wt. %, and content of the strong nitride-forming elements (Mo and Cr) thereof is 1.45 wt. %

The blank is nitrided using a gas nitriding method, wherein the nitriding temperature is 530° C., the nitriding time is 2 hours, the gas supply rate is 5 (the gas supply rate is gas supply amount per hour/in-furnace volume), and the nitriding gas is ammonia gas. N content of the nitrided tube is tested using the same testing method as that in Embodiment 1, and the measurement shows that the average N content is 0.10 wt. %. As the N content is obviously smaller than that of the strong nitride-forming elements, and the N elements are preferentially bonded with the strong nitride-forming elements to form a compound, the nitrided iron-based blank comprises a nitrogenous solid solution and an iron-based core portion, the solid solution coats the iron-based core portion, the compounds of the strong nitride-forming elements and the nitrogen elements are dispersively distributed in at least a part of the solid solution, and the iron-based core portion basically retains the microstructure and morphology before nitriding, namely an original iron alloy. In some cases, the content of the solid solution is obviously smaller than that of the dispersively distributed compound of the strong nitride-forming elements and the nitrogen elements, so that only the dispersively distributed compound of the strong nitride-forming elements and the nitrogen element can be effectively monitored. In addition, if nitriding degree is improved, for example, the nitriding time is prolonged and/or the nitriding temperature is improved, a uniform single structure can be also obtained, i.e. the compound of the dispersive strong nitride-forming elements and the nitrogen element are uniformly distributed. As the surface of the nitrided tube lacks a compact iron-nitrogen compound layer, not thermal treatment but a direct drawing is needed.

The above nitrided tube is drawn, with the drawing passes comprising multiple mandrel drawing and one mandrel-less drawing, and annealing passes may also be supplemented between the above drawing passes. The drawing passes adopted in the drawing include, successively: ① an outer mold of 5 mm and a mandrel of 4.4 mm are adopted for long mandrel drawing; ② an outer mold of 4.4 mm and a mandrel of 4.0 mm are adopted for long mandrel drawing; ③ annealing is conducted at the temperature of 600° C. for half an hour; ④ an outer mold of 3.5 mm and a mandrel of 3.19 mm are adopted for long mandrel drawing; ⑤ an outer mold of 2.3 mm and a mandrel of 2.02 mm are adopted for long mandrel drawing; ⑥ an outer mold of 1.795 mm and a mandrel of 1.627 mm are adopted for long mandrel drawing; ⑦ an outer mold of 1.590 mm is adopted for mandrel-less drawing.

In order to reduce the occurrence of drawing defects, the elongation coefficients for all the drawing passes do not exceed 2.0, which are preferably about 1.5. As a metal material has a certain elastic aftereffect, the outer diameter has certain resilience after the drawing with the outer mould of 1.590 mm, and actual measurements show that the outer diameter is 1.600 mm, and the wall thickness is 0.090 mm. After drawing, a tube which contains invariant components (the total alloy element content is smaller than or equal to 3 wt. %, wherein the total content of the strong nitride-forming elements is smaller than or equal to 0.05 wt. %) and having an outer diameter of 1.600 mm, a wall thickness of 0.090±0.005 mm and a hardness of 410 HV0.05/10 is obtained The above prefabricated tube after drawing is carried out laser cutting to obtain a coronary stent with a specification of 3.0*18 mm, wherein the cutting precision is ±5 μm. As the original material has been subjected to N element alloying treatment, the prefabricated tube prepared by drawing has high surface quality. Moreover, as the surface is free from the iron-nitrogen compound layer, chemical or electro-chemical polishing may be conducted directly to obtain a required stent. The laser-cut stent is polished to the size of the finished product (for example, width of the stent rod is 90 μm, and wall thickness of the stent is 50 μm), and no cracks can be observed from the inner and outer surfaces of the stent after it is polished. Measurements show that the radial strength of the stent is about 170 kPa, and the over-expanding plasticity is about 30%, thus meeting the requirements of medical devices and parts thereof (e.g., stents) for radial strength and plasticity.

Embodiment 5

A blank selected in this embodiment is a pure iron tube blank (with a total alloying element content being smaller than or equal to 0.5 wt. %, wherein the carbon content is smaller than or equal to 0.022%) having a size of 6*0.5 (the outer diameter is 6 mm, and the wall thickness is 0.5 mm).

The blank is nitrided using a gas nitriding method, wherein the nitriding temperature is 490° C., the nitriding time is 1 hour, the gas supply rate is 10 (the gas supply rate is gas supply amount per hour/in-furnace volume), and the nitriding gas is ammonia gas. The blank to be nitrided is of a fully annealed microstructure, and if the blank is of a deformation microstructure, the same effect can be obtained after a nitriding process is adjusted. The surface of the tube prepared through nitriding lacks a compact iron-nitrogen compound layer, including a uniform nitrogenous solid solution and an iron-nitrogen compound dispersively distributed in at least a part of the nitrogenous solid solution. N content of the nitrided tube is tested using the same testing method as that in Embodiment 1, and the measurement shows that the average N content is 0.02 wt. %.

As mentioned above, for the benefit of decomposition of the iron-nitrogen compound and uniform dispersive distribution of the nitrogen element, thermal treatment can be conducted on the nitrided tube, for example, the nitrided tube can be annealed at a temperature of 720° C. for 1 hour, and accordingly the nitrogen element can be distributed more uniformly. In the embodiment, in order to obtain a smaller average nitrogen content, the blank is only nitrided for 1 hour, at the moment, it is easy for the iron-nitrogen compound particles in the interior of the tube to grow, which is not conductive to obtaining a high-hardness prefabricated member, and therefore the blank can be rapidly cooled after thermal treatment, for example, the cooling rate is not less than 10 K/s. Cooling at this cooling rate can inhibit the growth of iron-nitrogen compounds in the cooling process, such that iron-nitrogen compounds in the prefabricated tube are finer and more diffused. As finer iron-nitrogen compounds produce better dispersion strengthening effects, a higher hardness can be obtained at a lower nitrogen content. Meanwhile, a lower nitrogen content can improve the over-expanding plasticity of medical devices (for example, luminal stents) prepared by this prefabricated tube.

The above nitrided tube is then drawn, with drawing passes comprising multiple mandrel drawing and one mandrel-less drawing, and annealing passes may also be supplemented between the above drawing passes. The drawing passes adopted in the drawing include, successively: ① an outer mold of 5 mm and a mandrel of 4.4 mm are adopted for long mandrel drawing; ② an outer mold of 4.4 mm and a mandrel of 4.0 mm are adopted for long mandrel drawing; ③ an outer mold of 3.5 mm and a mandrel of 3.2 mm are adopted for long mandrel drawing; ④ annealing is conducted at the temperature of 570° C. for 5 minutes; ⑤ rapid cooling is conducted, and the cooling rate is not less than 10 K/s; ⑥ an outer mold of 2.3 mm and a mandrel of 2.02 mm are adopted for long mandrel drawing; ⑦ an outer mold of 1.795 mm and a mandrel of 1.627 mm are adopted for long mandrel drawing; ⑧ an outer mold of 1.590 mm is adopted for mandrel-less drawing.

In order to reduce the occurrence of drawing defects, the elongation coefficients for all the drawing passes do not exceed 2.0, which are preferably about 1.5. As a metal material has a certain elastic after-effect, the outer diameter has certain resilience after the drawing with the outer mold of 1.590 mm, and actual measurements show that the outer diameter is 1.600 mm, and the wall thickness is 0.090 mm. After drawing, a tube which contains invariant components (the total impurity element content is smaller than or equal to 0.5 wt. %, wherein the carbon content is smaller than or equal to 0.022%) and having an outer diameter of 1.60 mm, a wall thickness of 0.090±0.005 mm and a hardness of 250 HV0.05/10 is obtained.

The above prefabricated tube after drawing is carried out laser cutting to obtain a coronary stent with a specification of 3.0*18 mm, wherein the cutting precision is ±5 μm. As the iron-based blank that has been subjected to N element alloying treatment is drawn, the prefabricated tube prepared therefrom has high surface quality. Moreover, as the iron-nitrogen compound layer on the surface is removed, chemical or electrochemical polishing may be conducted directly to obtain a required stent. The laser-cut stent is polished to the size of the finished product (for example, width of the stent rod is 90 μm, and wall thickness of the stent is 50 μm), and no cracks can be observed from the inner and outer surfaces of the stent after it is polished. Measurements show that the radial strength of the stent is about 110 kPa, and the over-expanding plasticity is about 40%, thus meeting the requirements of medical devices and parts thereof (e.g., stents) for radial strength and plasticity.

COMPARATIVE EXAMPLE

A pure iron tube blank which is the same as those in embodiments 1 and 3 is adopted, with a size of 6*0.5 (the outer diameter is 6 mm and the wall thickness is 0.5 mm), and the total impurity element content is smaller than or equal to 0.5 wt. %, wherein the carbon content is smaller than or equal to 0.022%. A blank stent is drawn directly, for example, the drawing passes adopted in the drawing include, successively: ① an outer mold of 5 mm and a mandrel of 4.4 mm are adopted for long mandrel drawing; ② an outer mold of 4.4 mm and a mandrel of 4.0 mm are adopted for long mandrel drawing; ③ an outer mold of 3.5 mm and a mandrel of 3.19 mm are adopted for long mandrel drawing; ④ an outer mold of 2.3 mm and a mandrel of 2.02 mm are adopted for long mandrel drawing; ⑤ an outer mold of 1.83 mm and a mandrel of 1.60 mm are adopted for long mandrel drawing; ⑥ an outer mold of 1.594 mm is adopted for mandrel-less drawing. In order to reduce the occurrence of drawing defects, the elongation coefficients for all the drawing passes do not exceed 2.0, which are preferably about 1.5. As a metal material has a certain elastic aftereffect, the outer diameter has certain resilience after the drawing with the outer mold of 1.594 mm, and actual measurements show that the outer diameter is 1.600 mm, and the wall thickness is 0.090±0.005 mm. Finally, after drawing, a prefabricated tube which contains invariant components (the total impurity element content is smaller than or equal to 0.5 wt. %, wherein the carbon content is smaller than or equal to 0.022%) and having an outer diameter of 1.60 mm, a wall thickness of 0.090±0.005 mm and a hardness of 280 HV0.05/10 is obtained.

The above prefabricated tube is laser-cut and polished to the size of a finished product (for example, width of the stent rod is 90 μm, and wall thickness of the stent is 50 μm), and no cracks can be observed from the inner and outer surfaces of the stent after it is polished. Measurements show that the radial strength of the stent is about 90 kPa, and the over-expanding plasticity is about 5%, and the stent rods of some tested stents are even broken in the process of being normally expanded to nominal diameters, thus not meeting the requirements of medical devices and parts thereof (e.g., stents) for radial strength and plasticity.

In the comparative example, the blank which is not subjected to alloying treatment is drawn directly, and the nitrogen content in the blank is almost negligible, so that the hardness of the prepared prefabricated tube only depends on work hardening of drawing, and the highest hardness can only be up to 300 HV0.05/10. While in embodiments 1 and 3, the tube added with the nitrogen elements is drawn to manufacture the prefabricated tube, the hardness of the prefabricated tube manufactured accordingly depends on the work hardening of drawing and also depends on solution strengthening of the nitrogen element and dispersion strengthening of the Fe—N compound, and the hardness of the prefabricated tube of embodiment 1 is 430 HV0.05/10, and the hardness of the prefabricated tube of embodiment 3 is 300 HV0.05/10. In addition, the blank which is not subjected to alloying treatment in the comparative example is poorer in plasticity, the surface quality of the prefabricated tube manufactured after drawing is poorer, obvious cracks can be seen, while in embodiments 1 and 3, the absorbable implanted medical device prefabricated tube has smaller adverse effects on the plasticity while satisfying the hardness which is the same as or even higher than that in the comparative example, and almost no obvious surface cracks are produced. On this basis, an absorbable implanted medical device prepared in accordance with embodiments 1 and 3 is obviously superior to an absorbable implanted medical device finished product in the comparative example in the aspects of radial strength, over-expanding plasticity and surface quality.

In conclusion, in the preparation method of the absorbable implanted medical device of the present disclosure, the iron-based blank (tube) is nitrided before forming the absorbable implanted medical device, with a high charging amount and a simple process, the production efficiency of the absorbable implanted medical device is improved, the rate of finished products is improved, and material loss is reduced. The lumen stent is taken as an example, with the advantages mentioned above, the radial strength and the over-expanding plasticity of the absorbable implanted stent prepared by the preparation method of the present disclosure satisfy the mechanical property of a conventional absorbable implanted stent.

In the preparation method of the preferred prefabricated tube of the present disclosure, the blank is nitrided before drawing, the plasticity of the iron-based tube can be improved accordingly, which is conductive to implementing a follow-up drawing process to improve the surface quality of the tube after drawing. The solid-solution strengthening and dispersion strengthening of nitrogen elements may further enhance the work-hardening effects produced by drawing, thus further improving hardening effects of the tube and improving the hardness of the tube after drawing. In another aspect, a white bright layer can be removed before drawing or no white bright layer is formed in the whole preparation method, so that a step of removing the white bright layer is not needed after a cutting or machining step. Even if there is a step of removing the white bright layer before drawing, it can also be removed by a thermal treatment method, thus exerting no influence on the size of the device after cutting or machining, reducing the difficulty in designing the device such as obtaining a specific radial dimension and surface smoothness, and avoiding the influence of the step of removing the white bright layer on the size of the device and surface performance.

It should be understood that the above data are numerical values in the embodiments of the present disclosure, the above numerical values are adjusted according to different specifications of specific products, and accordingly the embodiments are merely illustrative, but not intended to limit the present disclosure. The absorbable implanted medical device prefabricated tube and the absorbable implanted medical device prefabricated tube prepared by those skilled in the art based on the teachings of the present disclosure and the adopted preparation methods of the two are within the protection scope of the present disclosure.

The invention claimed is:

1. A method of preparing a prefabricated tube for an iron-based absorbable implanted medical device, comprising:
providing an iron-based blank; and
nitriding the iron-based blank up to an average nitrogen content of from 0.04 to 0.4 wt. % or from 0.02 to 0.04 wt. % to form a prefabricated tube.

2. The method of claim 1, further comprising:
after the providing step, and before the nitriding step, drawing the iron-based blank until the cross-sectional shape and the cross-sectional dimension of the iron-based blank are consistent with the cross-sectional shape and cross-sectional dimension of the iron-based absorbable implanted medical device prefabricated tube.

3. The method of claim 2, wherein the iron-based absorbable implanted medical device prefabricated tube has an outer diameter of 1 to 10 mm, and a wall thickness from 0.08 to 0.6 mm.

4. The method of claim 3, further comprising a plurality of drawing passes that includes at least one mandrel drawing and one mandrel-less drawing.

5. The method of claim 4, wherein the drawing coefficient of the at least one mandrel drawing is from 1.2 to 2.5, or the drawing coefficient in the at least one mandrel drawing is from 1.5 to 2.0, or the drawing coefficient in the mandrel-less drawing is about 1 or slightly greater than 1.

6. The method of claim 4, wherein the drawing passes are further supplemented by an annealing pass.

7. The method of claim 6, wherein the annealing temperature in the annealing pass is from 500° C. to 750° C.

8. The method of claim 6, wherein the annealing pass is followed by a cooling pass, and the cooling rate in the cooling pass is not less than 10 K/s.

9. The method of claim 1, further comprising heat-treating the nitrided iron-based blank.

10. The method of claim 9, further comprising, after heat-treating, cooling the nitrided iron-based blank, with the cooling rate in cooling being not less than 10 K/s.

11. The method of claim 1, wherein the iron-based blank is a pure iron with a content of all impurity elements being smaller than or equal to 0.5 wt. %; or an iron alloy with a content of all alloying elements being smaller than or equal to 3 wt. % and without strong nitride-forming elements; or an iron alloy with a content of all alloying elements being smaller than or equal to 3 wt. % and a total content of strong nitride-forming elements being greater than or equal to 0.05 wt. %.

12. The method of claim 11, wherein all the impurity elements in the pure ion and the iron alloy have a carbon content, and the carbon content of all the impurity elements in the pure iron is smaller than or equal to 0.022%; and the carbon content of all the alloying elements in the iron alloy is smaller than or equal to 0.45 wt. %.

13. A method of preparing an iron-based absorbable implanted medical device, comprising:
providing an iron-based blank;
nitriding the iron-based blank up to an average nitrogen content of from 0.04 to 0.4 wt. % or from 0.02 to 0.04 wt. % to form a prefabricated tube; and
molding-processing the prefabricated tube along the length direction into a plurality of iron-based absorbable implanted medical devices.

14. The method of claim 13, further comprising:
after the providing step, and before the nitriding step, drawing the iron-based blank until the cross-sectional shape and the cross-sectional dimension of the iron-based blank are consistent with the cross-sectional shape and cross-sectional dimension of the iron-based absorbable implanted medical device prefabricated tube.

15. The method of claim 14, wherein the iron-based absorbable implanted medical device prefabricated tube has an outer diameter of 1 to 10 mm, and a wall thickness from 0.08 to 0.6 mm.

16. The method of claim 15, further comprising a plurality of drawing passes that includes at least one mandrel drawing and one mandrel-less drawing.

17. The method of claim 16, wherein the drawing coefficient of the at least one mandrel drawing is from 1.2 to 2.5, or the drawing coefficient in the at least one mandrel drawing is from 1.5 to 2.0, or the drawing coefficient in the mandrel-less drawing is about 1 or slightly greater than 1.

18. The method of claim 16, wherein the drawing passes are further supplemented by an annealing pass.

19. The method of claim 18, wherein the annealing temperature in the annealing pass is from 500° C. to 750° C.

20. The method of claim 18, wherein the annealing pass is followed by a cooling pass, and the cooling rate in the cooling pass is not less than 10 K/s.

21. The method of claim 13, further comprising heat-treating the nitrided iron-based blank.

22. The method of claim 21, further comprising, after heat-treating, cooling the nitrided iron-based blank, with the cooling rate in cooling being not less than 10 K/s.

23. The method of claim 13, wherein the iron-based blank is a pure iron with a content of all impurity elements being smaller than or equal to 0.5 wt. %; or an iron alloy with a content of all alloying elements being smaller than or equal to 3 wt. % and without strong nitride-forming elements; or an iron alloy with a content of all alloying elements being smaller than or equal to 3 wt. % and a total content of strong nitride-forming elements being greater than or equal to 0.05 wt. %.

24. The method of claim 23, wherein all the impurity elements in the pure ion and the iron alloy have a carbon content, and the carbon content of all the impurity elements in the pure iron is smaller than or equal to 0.022%; and the carbon content of all the alloying elements in the iron alloy is smaller than or equal to 0.45 wt. %.

* * * * *